United States Patent

Chou

[11] Patent Number: 6,049,728
[45] Date of Patent: *Apr. 11, 2000

[54] METHOD AND APPARATUS FOR NONINVASIVE MEASUREMENT OF BLOOD GLUCOSE BY PHOTOACOUSTICS

[75] Inventor: Mau-Song Chou, Rancho Palos Verdes, Calif.

[73] Assignee: TRW Inc., Redondo Beach, Calif.

[*] Notice: This patent is subject to a terminal disclaimer.

[21] Appl. No.: 09/190,940

[22] Filed: Nov. 12, 1998

Related U.S. Application Data

[63] Continuation of application No. 08/978,317, Nov. 25, 1997.

[51] Int. Cl.$^7$ .................................................... A61B 5/00
[52] U.S. Cl. ........................... 600/316; 600/310; 600/322; 374/45
[58] Field of Search .................................. 600/309, 310, 600/316, 322; 374/45

[56] References Cited

U.S. PATENT DOCUMENTS 5,348,002  9/1994  Caro .

FOREIGN PATENT DOCUMENTS

| 12810 | 9/1988 | Australia . |
| 0282234 | 9/1988 | European Pat. Off. . |
| 2728452 | 6/1996 | France . |
| 9118548 | 12/1991 | WIPO . |

OTHER PUBLICATIONS

Spanner, G., Niessner, R.: "Noninvasive Determination Of Blood Constituents Using An Array Of Modulated Laser Diodes And A Photoacoustic Sensor Head," Fresenius Journal of Analytical Chemistry, vol. 355, No. 3/4, Jun. 1996, p. 327/328 XP002066087.

Rosencwaig, A., "Photoacoustic Spectroscopy—A New Tool for Investigation of Solids", May 1975, pp. 592–604, Analytical Chemistry, vol. 47, No. 6.

Vargas, H., et al., "Photoacoustic and Related Photothermal Techniques", Jul. 1987, pp. 44–101, Physics Reports 161, No. 2.

Nordal, Per–Erik, et al., "Photoacoustic Spectroscopy on Ammonium Sulphate and Glucose Powders and Their Aqueous Solutions Using A CO2 Laser", Aug. 1977, pp. 185–189, Optics Communications, vol. 22, No. 2.

Patel, C., et al., "Pulsed Optoacoustic Spectroscopy of Condensed Matter", Jul. 1981, pp. 517–550, Reviews of Modern Physics, vol. 53, No. 3.

Poulet, P., et al., "In Vivo Cutaneous Spectroscopy by Photoacoustic Detection", Nov. 1985, pp. 585–588, Medical & Biological Engineering & Computing, vol. 23.

(List continued on next page.)

*Primary Examiner*—Eric F. Winakur
*Attorney, Agent, or Firm*—Michael S. Yatsko

[57] ABSTRACT

A method and apparatus for noninvasively measuring blood glucose levels provides an indirect, reagentless, differential, photoacoustic technique which responds to absorption in a thin surface layer. An excitation source provides electromagnetic energy which is utilized to irradiate the tissue, such as skin. The output of the radiation of the excitation source at the desired wavelength is coupled through a transmission device, such as a fiber optic bundle, which irradiates the electromagnetic energy onto the body surface. Upon irradiation, acoustic energy is generated by the absorption of the electromagnetic energy in a relatively thin layer of the sample to be measured, characterized by a heat-diffusing length. The acoustic energy is detected by the probe which includes a measuring cell, reference cell, window and differential microphone. Absorption of the light beam results in periodic heating of the tissue, at and near the tissue surface. The air in contact with the tissue surface in the measuring cell is in turn heated, and produces an acoustic emission in the measuring cell. This acoustic emission is detected with the differential microphone, one end of which is positioned in the measuring cell and the other end of which is positioned in the reference cell. A processor determines the concentration of the substance based upon the detected acoustic signal.

57 Claims, 4 Drawing Sheets

OTHER PUBLICATIONS

Kolmel, K., et al., "Evaluation of Drug Penetration into the Skin by Photoacoustic Measurement", Sep./Oct. 1986, pp. 375–385, J. Soc. Cosmet. Chem., vol. 37.

Marbach, R., et al., "Optical Diffuse Reflectance Accessory for Measurements of Skin Tissue by Near–Infrared Spectroscopy", Feb. 1995, pp. 610–621,Applied Optics, vol. 34, No. 4.

Heise, H., "Non–Invasive Monitoring of Metabolites Using Near Infrared Spectroscopy: State of the Art", Jul. 1996, pp. 527–533, Horm. Metab. Res. 28.

Drapcho, D., et al., "Digital Signal Processing for Step–Scan Fourier Transform Infrared Photoacoustic Spectroscopy", 1997, pp. 453–460, Applied Spectroscopy, vol. 51, No. 4.

Jones, R., et al., Quantitative Depth Profiling of Layered Samples Using Phase–Modulation FT–IR Photoacoustic Spectroscopy, 1996, pp. 1258–1263, Applied Spectroscopy, vol. 50, No. 10.

Freiherr, G., "The Race to Develop a Painless Blood Glucose Monitor", Mar. 1997, pp. 58–64, Medical Device & Diagnostic Industry.

Jiang, E., et al., "Comparison of Phase Rotation, Phase Spectrum, and Two–Dimensional Correlation Methods in Step–Scan Fourier Transform Infrared Photoacoustic Spectral Depth Profiling", May 15, 1997, pp. 1931–1935, Analytical Chemistry, vol. 69, No. 10.

Crocombe, R., et al., "The Design, Performance and Applications of a Dynamically–Aligned Step–Scan Interferometer".

METHOD AND APPARATUS FOR NONINVASIVE MEASUREMENT OF BLOOD GLUCOSE BY PHOTOACOUSTICS A. 35 U.S.C. §§ 120, 121 and 365(c)

This application is a continuation of copending application application Ser. No. 08/978,317 filed on Nov. 25, 1997.

BACKGROUND OF THE INVENTION

The present invention relates generally to measurement devices, and more particularly to noninvasive measurement of blood glucose by photoacoustics.

An estimated 16 million Americans (approximately 7% of the total population in the United States) have diabetes, a disease which can cause severe damage to the heart, kidneys, eyes and nerves. Diabetics need to monitor their blood glucose levels frequently, often as much as six times a day, to maintain a proper level of insulin in their blood. Intense testing and treatment of diabetes can reduce the complications, including blindness, kidney failure and heart attack, by as much as 70%.

A well-known invasive procedure for monitoring blood glucose levels involves pricking the finger of a patient to obtain a blood sample, and analyzing it for glucose content by the use of an enzyme-based method. This invasive method, which is painful and has risk of infection, often prevents the patient from performing the needed frequent testing and treatment. Additionally, because finger-stick monitoring is an enzyme-based technique, the cost for this technique is high.

Techniques which rely on non-invasive monitoring of glucose generally utilize infrared or near infrared technology to noninvasively obtain optical signatures indicating the level of glucose. Some of these infrared techniques rely on direct photoacoustic generation methods for noninvasive monitoring. In direct photoacoustic generation methods, the acoustic wave is produced in a sample where the excitation beam is absorbed. For example, U.S. Pat. No. 5,348,002 to Caro discloses a device for measuring blood glucose which includes a light source for applying electromagnetic radiation to tissue under analysis and a transducer for detecting acoustic energy. The transducer is positioned on one side of the finger and the incoming electromagnetic wave impinges on the other side of the finger, opposite the transducer. This technique is generally unreliable because a tissue, such as a body part, is optically thick. The impinging electromagnetic energy is almost totally absorbed by the tissue. Consequently, the measured acoustic wave will respond to the total incident electromagnetic energy—not just the fraction absorbed by glucose.

The technique disclosed in Caro also fails to compensate for the adverse effects caused by the absorption of radiation by water, rather than the medium to be measured, such as glucose. The effect of strong water absorption is twofold. First, because tissue has a high percentage of water, water absorption can prevent a light beam from penetrating a sufficient depth through tissue. Second, water absorption can yield an acoustic signal which is overwhelming compared to that from glucose. In particular, when electromagnetic energy impinges on water at certain wavelengths, the water optically absorbs the electromagnetic energy, inducing a temperature rise and related pressure variations in the tissue. The pressure changes caused by water are transmitted to the transducer as a series of pulses or waves, thus overwhelmingly interfering with the measurement of glucose.

Another photoacoustic method for direct, non-invasive monitoring of glucose which also fails to address the adverse effects caused by the absorption of radiation by water is described in EP 0 282 234, which discloses a technique for measuring blood glucose utilizing a transducer for monitoring acoustic energy. In EP 0 282 234, a semiconductor laser operating in the wavelength range of about 1300 to 1580 nm is utilized to excite glucose in a blood stream to generate acoustic energy. At this wavelength range, water absorption can adversely affect glucose measurements. As with other direct photoacoustic techniques, for accurate measurements, the medium must be optically thin. Unfortunately, most tissue in any body part is optically thick.

Other recent noninvasive devices for monitoring blood glucose suffer from shortcomings as well. One such device, referred to as the "Dream Beam", developed by Futrex Medical Instrumentation, Inc. of Gaithersburg, Md. and disclosed in U.S. Pat. Nos. 5,028,787, 5,077,376 and 5,576,544, includes a battery-operated box about the size of a television remote control designed to provide noninvasive glucose measurements with the use of infrared radiation. Infrared light, having a wavelength between about 600 and 1000 nm, is passed through a finger. This approach has failed to produce accurate measurements as well.

Another noninvasive device, referred to as the "Diasensor 1000", developed by Biocontrol Technology, Inc. of Pittsburgh, Pa. and disclosed in U.S. Pat. No. 5,070,874, has failed to produce accurate results as well. In this device, a tabletop spectrophotometer is designed to recognize a person's glucose patterns through the use of a light beam that passes through the skin of the forearm into the blood and is then reflected back to a sensor. A microprocessor is intended to interpret the data and calculate the blood glucose level. This reflection technique suffers from numerous shortcomings, including a small return signal, scattering from tissue (which reduces the signal and increases fluctuation) and interferences by strong background light.

As of date, no noninvasive glucose monitors, including the devices discussed above, have been approved by the Federal Drug Administration. This is mainly because current methods, which rely in large part on optical transmission or reflection, generally do not have sufficient sensitivity. In particular, absorption by glucose molecules is extremely weak compared to other blood constituents. Consequently, the return signal which is generated by other blood constituents is overwhelming compared to that by glucose, resulting in inaccurate measurements. Additionally, these optical techniques are severely limited by noise induced by light scattering through the tissue and cell walls. A sophisticated chemometric data process algorithm is often required to suppress such noise.

What is needed therefore is an apparatus and method for monitoring blood glucose which is painless, noninvasive, accurate and economical.

SUMMARY OF THE INVENTION

The preceding and other shortcomings of the prior art are addressed and overcome by the present invention which provides an apparatus for determining a concentration of a component in a first medium, including a source for irradiating a portion of the first medium by heat-diffusion to generate acoustic energy propagating in a second medium over a surface of the first medium in response to the irradiation, a detector for detecting the acoustic energy and providing an acoustic signal in response to the acoustic energy and a processor for determining the concentration of the component in response to the acoustic signal and characteristics of the component.

In another aspect, the present invention provides a method for determining a concentration of a component in a first medium, including the steps of irradiating a portion of the first medium by heat-diffusion to generate acoustic energy propagating in a second medium over a surface of the first medium in response to the irradiation, detecting the acoustic energy and providing an acoustic signal in response to the acoustic energy and determining the concentration of the component in response to the acoustic signal and characteristics of the component.

In still another aspect, the present invention provides an apparatus for measuring a concentration of an analyte in a first medium, including a source for providing electromagnetic energy at wavelengths corresponding to the absorption characteristics of the analyte to excite a portion of the first medium by heat-diffusion to generate acoustic energy propagating in a second medium in response to the excitation, a detector for detecting the acoustic energy and providing an acoustic signal in response to the acoustic energy and a processor for determining the concentration in response to the acoustic signal and absorption spectrum of the analyte.

In a further aspect, the present invention provides a method for measuring a concentration of an analyte in a first medium, including the steps of providing electromagnetic energy at wavelengths corresponding to the absorption characteristics of the analyte to excite a portion of the first medium by heat-diffusion to generate acoustic energy propagating in a second medium in response to the excitation, detecting the acoustic energy and providing an acoustic signal in response to the acoustic energy and determining the concentration in response to the acoustic signal and absorption spectrum of the analyte.

In another aspect, the present invention provides an apparatus for determining a concentration of glucose in a body part, including a source for irradiating a portion of the body part by heat-diffusion to generate acoustic energy propagating in air over a surface of the body part in response to the irradiation, a detector for detecting the acoustic energy and providing an acoustic signal in response to the acoustic energy and a processor for determining the concentration of glucose in response to the acoustic signal and characteristics of glucose.

In a further aspect, the present invention provides a method for determining a concentration of glucose in a body part, including the steps of irradiating a portion of the body part by heat-diffusion to generate acoustic energy propagating in air over a surface of the body part in response to the irradiation, detecting the acoustic energy and providing an acoustic signal in response to the acoustic energy and determining the concentration of glucose in response to the acoustic signal and characteristics of glucose.

The foregoing and additional features and advantages of this invention will become apparent from the detailed description and accompanying drawing figures below. In the figures and the written description, numerals indicate the various features of the invention, like numerals referring to like features throughout for both the drawing figures and the written description.

DETAILED DESCRIPTION OF THE PREFERRED EMBODIMENTS

Figure 1:
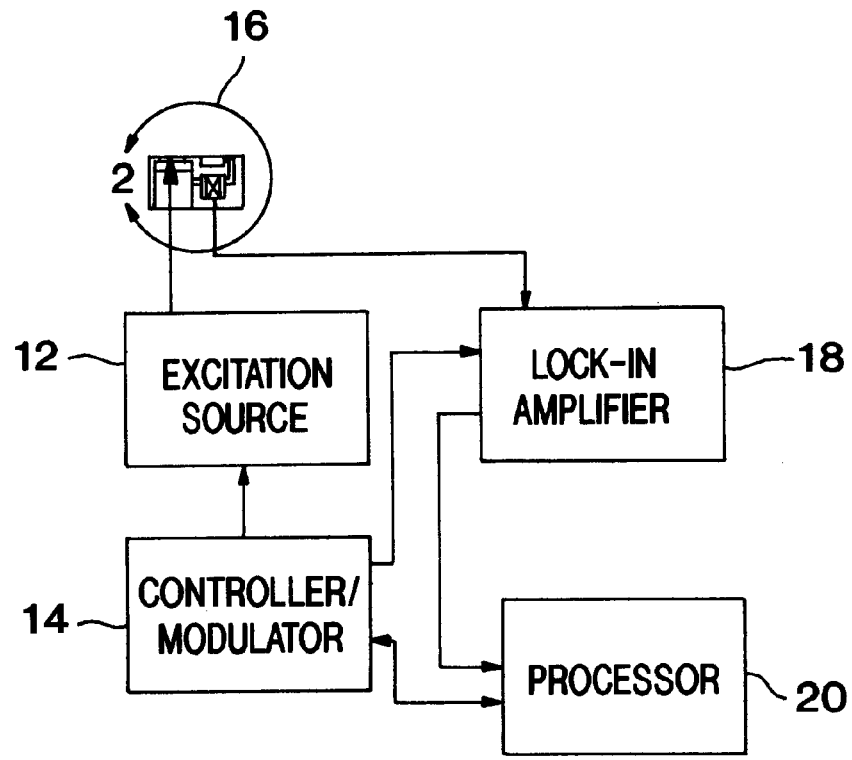
FIG. 1 is a diagram of a noninvasive photoacoustic measurement device in accordance with a preferred embodiment of the present invention.

Referring to FIG. 1, a noninvasive photoacoustic system 10 for measuring a concentration of a sample is illustrated. The noninvasive photoacoustic system 10 of the present invention is preferably utilized to measure blood glucose levels and provides an indirect, reagentless, differential, photoacoustic technique which responds to absorption in a thin surface layer. In particular, in the present invention, only absorption in a relatively thin layer of the sample to be measured, characterized by a heat-diffusing length, is responsible for generation of an acoustic emission. The indirect photoacoustic system 10 of the present invention can thus be used to probe the absorption of a sample even under optically thick conditions.

The present invention is not limited to the measurement of blood glucose levels, but may also be utilized to measure the concentration of other substances or analytes, particularly those in human body tissue. For example, the present invention can be utilized to monitor adenosine triphosphate, blood alcohol, blood gas, hemoglobin, cholesterol and various ions in blood streams, and drugs of abuse.

Figure 2:
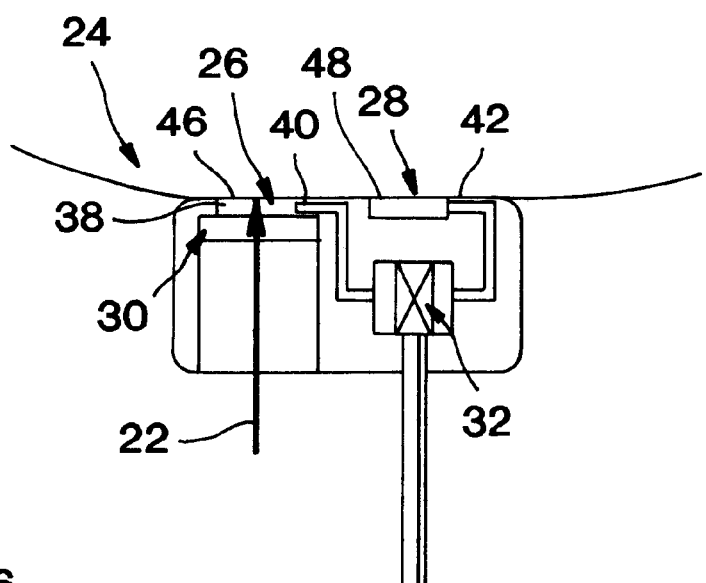
FIG. 2 is a detailed diagram of the probe illustrated in FIG. 1.

As is illustrated in FIGS. 1 and 2, the photoacoustic system 10 includes an excitation source 12, controller/modulator 14, probe 16, lock-in amplifier 18 and processor 20 for measuring the concentration of a sample, such as glucose. The excitation source provides electromagnetic energy which is utilized to irradiate the tissue, such as skin. The output of the radiation of the excitation source 12 at the desired wavelength is coupled through a transmission device 22, such as a fiber optic bundle, which irradiates the electromagnetic energy onto the body surface 24. The present invention is not limited to utilization of the transmission device 22. Rather, the output of the radiation of the excitation source 12 can be transmitted directly to the body surface 24 or indirectly through the transmission device 22. For illustrative purposes, however, a transmission device 22 in the form of a fiber optic bundle will be utilized. Upon irradiation, acoustic energy is generated by the absorption of the electromagnetic energy in a relatively thin layer of the sample to be measured, characterized by a heat-diffusing length as discussed in detail below.

As is illustrated in detail in FIG. 2, the acoustic energy is detected by the probe 16 which includes a measuring cell 26, reference cell 28, window 30 and differential microphone 32. An acoustic wave is generated in the measuring cell 26 by heat transfer from the thin layer of irradiated tissue 24. In particular, the output of the radiation is coupled through the transmission device 22, such as a fiber-optic bundle, which irradiates a sample, such as tissue. Absorption of the light beam results in periodic heating of the tissue, at and near the tissue surface 24. The radiation is focused on the tissue surface through the window 30 of the measuring cell 26. The measuring cell 26 is air-tight sealed on one end with the window 30 mounted over the measuring cell opening. The window 30 is preferably manufactured from a suitable material selected for transmission of light from the excitation source 12. Since the laser beam is modulated at certain frequencies, the temperature of the tissue is also modulated at the same frequency in the region where the laser beam is incident. The air 38 in contact with the tissue surface 24 in the measuring cell 26 is in turn heated periodically at the same modulated frequency. Because of this periodic temperature variation of the air in the measuring cell 26, the air expands and contracts periodically, thus generating a periodical acoustic wave at the same modulated frequency in the measuring cell 26. This acoustic wave is detected with the differential microphone 32, one end 40 of which is positioned in the measuring cell 26 and the other end 42 of which is positioned in the reference cell 28. Absorption of the light in the air 38 itself is minimal, and therefore substantially all heating arises from absorption of the light in the thin layer of irradiated tissue 24.

The measuring and reference cells 26 and 28 are preferably air cells which are closely-spaced to one another, typically having their outer rims positioned within 1 mm to 1 cm from each other, far enough apart such that radiation will not diffuse from one cell to the other. The ends 40 and 42 of the measuring and reference cells 26 and 28, respectively, are formed by the surface 24 of a body part. The rims of the cells 26 and 28 are preferably pressed to the body surface 24 to form substantially sealed spaces within each respective cell 26 and 28. The differential cells 26 and 28 prevent overloading of the lock-in amplifier 18 from bodily noise, typically generated from muscle spasms and/or pulsative bloodflow through subcutaneous vessels. Each cell 26 and 28 has its acoustic outlet 40 and 42, respectively, connected with a sound port of the differential microphone 32 which measures the difference in acoustic response from the two closely-spaced cells 26 and 28 as they are pressed against the body surface 24. A photoacoustic signal is generated in the measuring cell 26 by irradiation of the body surface 24. In operation, the measuring cell 26 is thus, upon irradiation of the body surface 24, positioned over a laser irradiated body surface 46 and the reference cell 28 is positioned over a non-laser irradiated body surface 48. Bodily noise, which may at times be generated in both cells 26 and 28, is suppressed by the differential microphone 32. In particular, the noise signals from both the measuring and reference cells 26 and 28, typically almost the same with respect to magnitude and phase, are canceled out by the differential microphone 32. The differential microphone 32 thus separates the acoustic signal from the background noise.

The detected signals from the probe 16 are then applied to the lock-in amplifier 18 which records and averages the output signal from the differential microphone 32. The lock-in amplifier 18 also extracts from the output signal only those signals which have the same frequency component as the modulation frequency of the irradiated light generated by the excitation source 12 under the control of the controller/modulator 14. The frequency component extracted is then applied to processor 20, typically a microprocessor data acquisition system. The processor 20 may implement a frequency domain analysis to analyze the temporal frequency response of the extracted acoustic signal in order to improve the signal to noise ratio. A chemometric spectral analysis technique may also be utilized to deduce the observed photoacoustic spectrum to improve the detection limit and accuracy.

The photoacoustic system 10 of the present invention measures glucose within a characteristic heat-diffusion length from the surface 24 of a medium, such as a body part i.e. skin. The heat diffusion length is defined in accordance with the following equation:

$$\text{Diffusion length} = (D/\pi f)^{0.5} \quad (1)$$

where

D=thermal diffusivity ($cm^2/s$)

f=modulation frequency of excitation source (Hz)

$\pi$=3.14159265 (constant)

Diffusivity (D) is defined in accordance with the following equation:

$$D = k/(\rho c) \quad (2)$$

where k=thermal conductivity (cal/cm-s-° C.)

c=heat capacity of the material (cal/g-° C.)

$\rho$=density of the material ($g/cm^3$)

For example, according to equation (2), assuming a heat capacity (c) of 0.8 cal/g-° C. and a thermal conductivity (k) of 0.0015+/−0.003 cal/cm-s-° C. at 23–25° C., the diffusivity (D) of a typical skin would be about $7\times10^{-4}$ $cm^2/s$. According to equation (1), for a thermal diffusivity (D) of about $7\times10^{-4}$ $cm^2/s$ for a typical skin and a diode laser having a modulation frequency (f of 1 Hz, the heat diffusion length of a typical skin would be about 150 $\mu$m. Thus, a diffusion length of about 100 to 200 $\mu$m can be achieved with a suitable selection of the frequency of the irradiated light.

The present invention is thus particularly useful for monitoring in those areas of the body in which the stratum corneum is relatively thin and glucose can be accessed within the thin layer below the tissue surface. The inner lip is a preferred body part because its mucosal membrane is relatively thin, typically in the range of about 50–100 $\mu$m. Glucose in interstitial fluid or capillary blood vessels beneath the mucosal membrane can thus be accessed within about 100 to 200 $\mu$m of an estimated diffusion length as discussed above. Since glucose in interstitial fluid is generally equilibrated well with that in blood, the present invention may be utilized to measure glucose in the interstitial fluid as well as in the capillary blood vessels.

The present invention is relatively immune to turbid conditions. In particular, although the incident light may be diffused by scattering mediums, such as red blood cells, tissue and blood vessel walls, the optical absorption process continues as does the photoacoustic generation. Although the presence of scatter may increase the radius of the interactive region, the photoacoustic response should remain nearly the same. This is particularly important since biological tissue is a medium which tends to highly scatter light.

The excitation source 12 is preferably operable at wavelengths which coincide with the wavelengths where absorption of the substance to be measured is relatively strong and the absorption of any interfering substances, such as water, is relatively weak. For example, referring to the graph 34 in FIG. 3, for determining the concentration of glucose in a bloodstream, the excitation source 12 is preferably tuned to the absorption bands of glucose in the spectral ranges from about 1520–1850 nm and about 2050–2340 nm to induce a strong photoacoustic emission. In these wavelength ranges, water absorption is relatively weak and glucose absorption is relatively strong. Thus, in accordance with the present invention, even though tissue may have a high percentage of water, at the above-specified wavelength regions, the electromagnetic radiation is able to penetrate through the tissue to a sufficient depth to allow for accurate measurements. Despite water absorption, the acoustic signal which is generated by the absorption of electromagnetic radiation by glucose is not overwhelmed by that generated by water. In particular, when electromagnetic energy impinges on glucose at the above-specified wavelengths, the glucose optically absorbs the energy, inducing a temperature rise and generating an acoustic emission indirectly in the air. The acoustic emission caused by the glucose is transmitted to the microphone as a series of pulses or waves.

Referring to FIG. 1, the excitation source 12 may be a plurality of laser diodes. A laser diode is generally preferable due to its compact size and low cost. Since the tunable wavelength range of a diode laser may not be large enough to accommodate the desired wavelength ranges of operability, in some cases, such as for the measurement of the concentration of glucose, a plurality of laser diodes each having variable tunable wavelengths may be utilized to generate electromagnetic energy to correspond with the wavelength regions where absorption is strongest. In such case, the resulting beam from the diodes is delivered directly or through the transmission device 22, such as a fiber optic bundle, to irradiate the body surface 24 as shown in FIG. 2. The transmission device 22 is not limited to a fiber optic bundle, but rather may be any waveguide which enables the electromagnetic radiation generated by the excitation source 12 to be reliably transmitted to the body surface 24.

Additionally, the present invention is not limited to the use of one or more diode lasers as the excitation source 12. Rather, the present invention may take advantage of conventional or newly-developed coherent and non-coherent light sources as well as solid-state devices. Such known sources include, but are not limited to, light emitting diodes (LED), optical parametric oscillator lasers (OPO), Fourier Transformed Infrared (FTIR) based light sources and other non-coherent light sources such as heated wires and lamps. OPO lasers are discussed in "Optical Parametric Oscillators", Laser Handbook, by E. Smith, F. T. Arecchi and E. O. Schultz-Dubois (North Holland Amsterdam, 1972), volume I, pages 837–895. FTIR based continuous light sources are discussed in "Quantitative Depth Profiling of Layered Samples Using Phase-Modulation FTIR Photoacoustic Spectroscopy", by Roger W. Jones and John F. McClelland, Applied Spectroscopy, Volume 50, Number 10, 1996. As with the use of a plurality of diode lasers, it may be desirable to use one or more light sources in combination to produce the desired spectrum of wavelengths.

The examples provided herein are to illustrate specific instances of the practice of the invention and are not to be construed as limiting the present invention to these examples.

Figure 3:
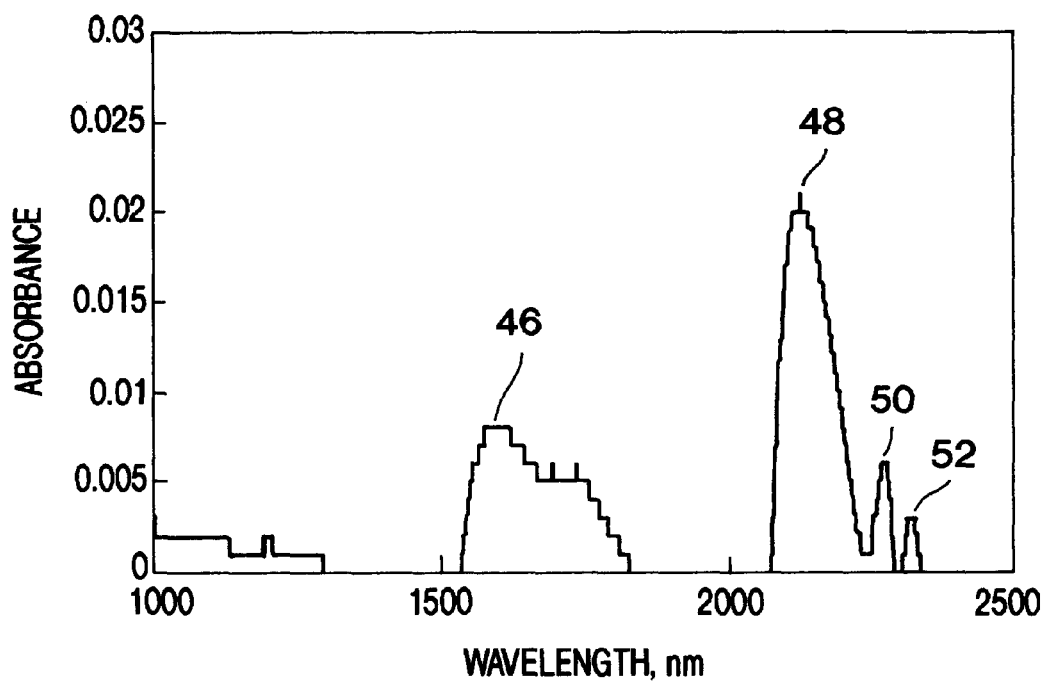
FIG. 3 is a graph showing the absorption spectrum of glucose derived from a 0.75-M glucose/water solution.

Referring to FIG. 3, a graph 34 of the absorption spectrum of glucose derived from a 0.75-M (or 13.5 g/dl) glucose/water solution is illustrated. The absorption spectrum of glucose was measured in order to determine suitable laser wavelengths for glucose measurements. In particular, a Fourier Transform Infrared (FTIR) spectrometer, in this case a Galaxy Model 7600 by Mattson Instruments of Madison, Wis., with a spectral resolution of 2 $cm^{-1}$, was used to measure the absorption spectrum of a glucose/water solution in a 0.5-mm-pathlength cell. The absorption spectrum of glucose illustrated in FIG. 3 was derived by subtracting the absorbance of water alone from that of the glucose solution. The two relatively strong peaks 46 and 48 of glucose absorption are at about 1600 and 2120 nm, and the two weaker peaks 50 and 52 are at about 2270 and 2320 nm.

Figure 4:
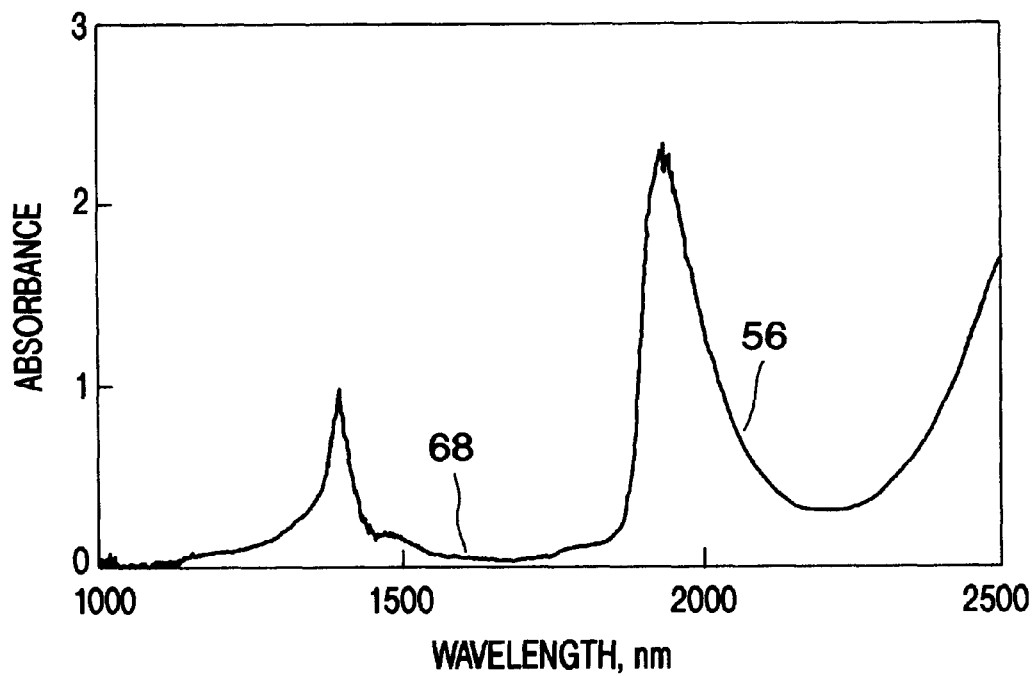
FIG. 4 is a graph showing the absorption spectrum of water.

Referring to FIG. 4, a graph 54 of the absorption spectrum of water is illustrated. The glucose absorption peaks, shown in FIG. 3, fall within the water absorption transmission windows. Even in the water transmission windows, absorption by water is much stronger than that by glucose in the concentration range of interest. Based on FIG. 4, the absorption depth of water 56 and 68 is about 0.57 and 4.8 mm at about 2120 and 1600 nm, respectively. The absorption depth is defined as the distance at which the incident light is reduced by 1/e (where e=the base of the system of natural logarithms having the approximate numerical value 2.71828). As long as the absorption depth is larger than the estimated heat diffusing length, effective measurements can be made.

Figure 5:
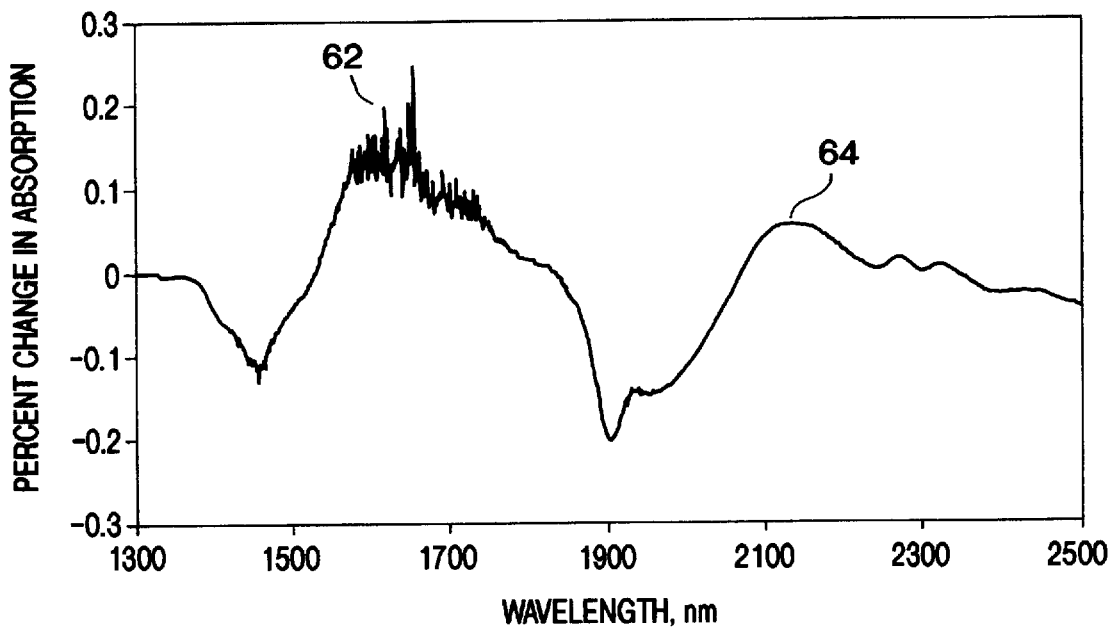
FIG. 5 is a graph showing estimated percentage changes in absorption of a 100 mg/dl glucose/water solution over water.

Referring to FIG. 5, a graph 60 of the percentage change in absorption of a 100 mg/dl glucose/water solution, as estimated from that at a 7.5-M glucose/water solution shown in FIG. 3, over that of water alone (FIG. 4), is illustrated. The positive value indicates increase in absorption due to the presence of glucose. The negative value indicates decrease in water absorption due to substitution of water molecules by glucose. The increase reaches a maximum 62 of about 0.12% at 1600 nm and another maximum 64 of about 0.057% at 2120 nm. Referring to FIGS. 3 and 5, although the absorption peak 48 at 2120 nm for glucose is stronger than the absorption peak 46 at 1600 nm, the absorption peak 46 at 1600 nm peak may yield a higher sensitivity because of the higher percentage 62 (by about a factor of 2.1) over water absorption as shown in FIG. 5.

One skilled in the art will recognize that the present invention is directed towards providing an indirect, photoacoustic technique which responds to absorption in a thin surface layer and is not limited to the configuration illustrated in FIG. 1. In particular, in accordance with another embodiment of the invention, the present invention may be adapted to be utilized with a microphone positioned above the surface for detecting the acoustic wave. Additionally, the present invention is not limited to the use of a lock-in amplifier for extracting the detected acoustic signal from interfering signals, such as background noise signals. Rather, a digital oscilloscope or other data acquisition devices may be utilized to average the acoustic signal and then differentiate it from any interfering signals.

Figure 6:
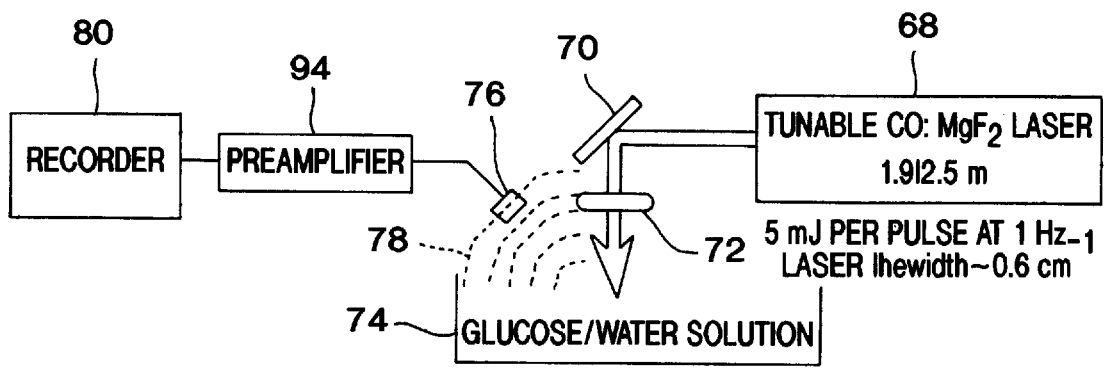
FIG. 6 is a diagram showing a laboratory arrangement for noninvasive photoacoustic measurements of glucose in a glucose/water solution.

In operation, the present invention may be utilized to provide photoacoustic measurements of glucose/water solutions at various glucose concentrations, as illustrated in the laboratory arrangement of the present invention 66 shown in FIG. 6. A $Co:Mg:F_2$ laser 68 by Schwartz Electro-Optics, Inc. of Orlando, Fla., provides an output wavelength tunable from about 1900 to 2500 nm was utilized as the excitation source. The laser 68, which is pulsed at about 1 Hz, is directed by a tuning mirror 70 and then focused by a lens 72 into a glucose/water solution 74 in a 50-ml glass beaker. A microphone 76, positioned in the air above the glucose/water solution 74, is used to monitor the resulting acoustic wave 78, generated indirectly as discussed above. The output from the microphone 76 is applied to a preamplifier 94 for amplification. The amplified signal is then applied to a recorder 80, in this case a digital oscilloscope by Tektronix of Wilsonville, Oreg., for recordation and averaging for about 20 pulses at each wavelength setting.

Figure 7:
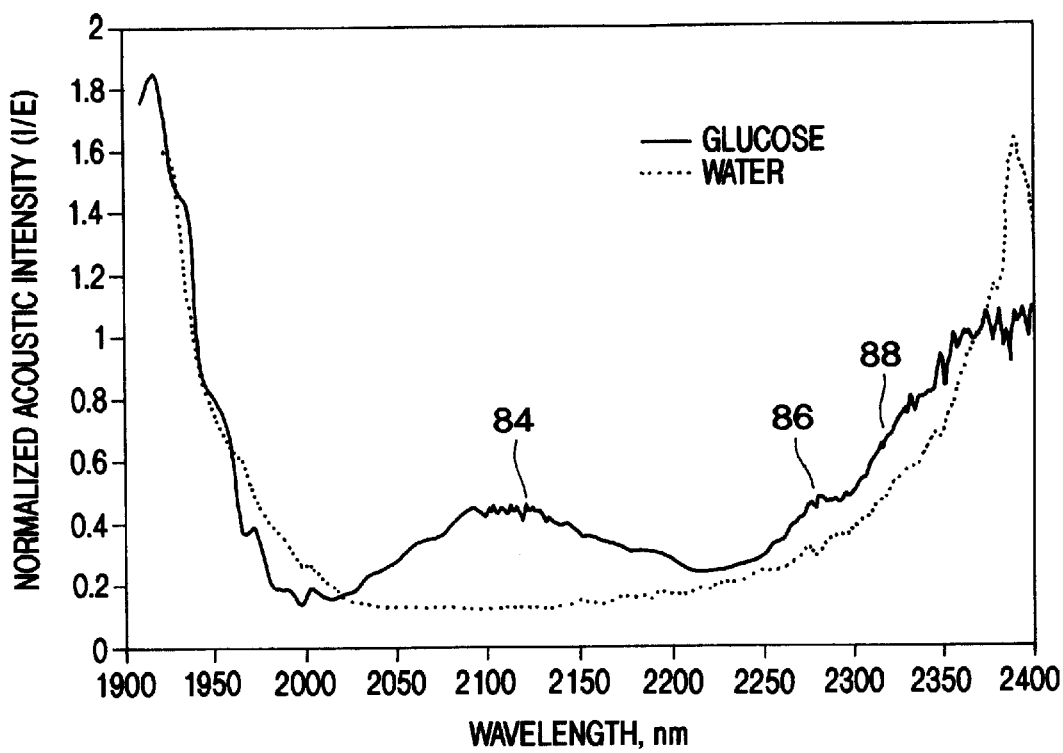
FIG. 7 is a graph showing a photoacoustic spectra of a saturated glucose/water solution and of water, generated from the measurement device illustrated in FIG. 6.

Results of the measurements made by the present laboratory arrangement 66 are illustrated in the graph 82 shown in FIG. 7. The normalized acoustic intensity is given as I/E, where I is the peak of the acoustic intensity and E is the incident laser energy. Glucose has a relatively broad and strong peak 84 at about 2120 nm, and two weaker peaks 86 and 88 at about 2270 and 2320 nm, respectively. These peaks 84, 86 and 88 are consistent with that expected from the glucose absorption spectrum as shown in FIG. 3. The present invention can thus be utilized to measure glucose even under an optically thick condition.

Figure 8:
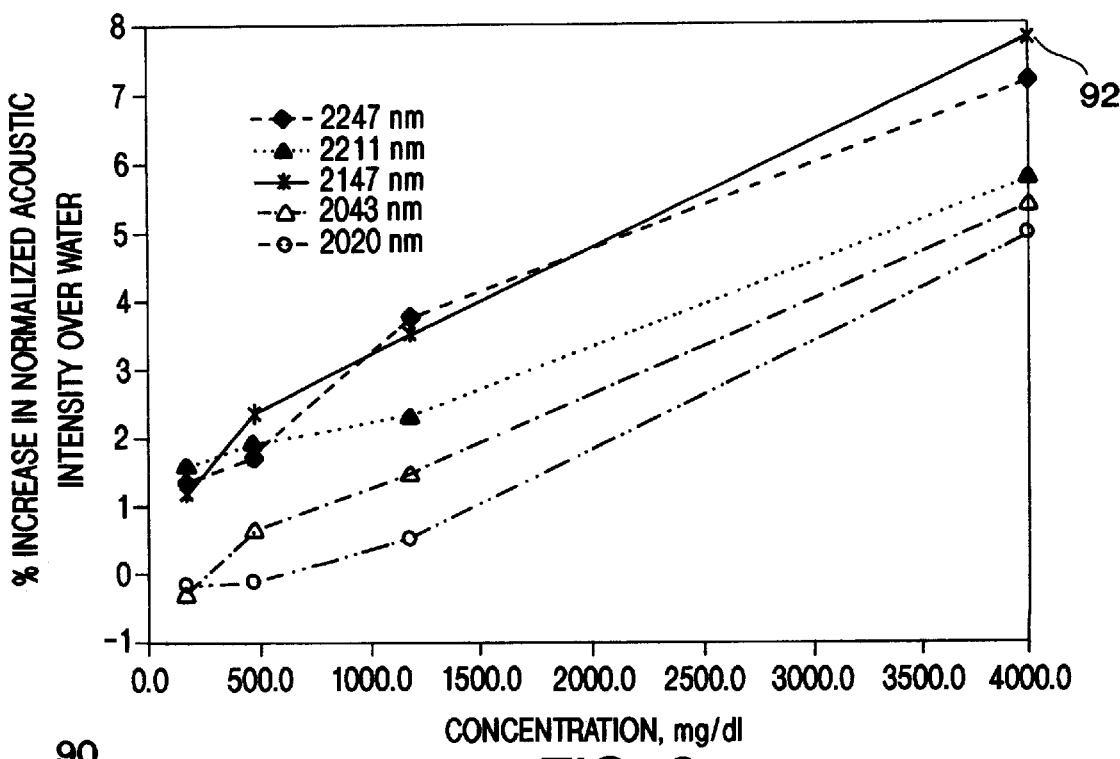
FIG. 8 is a graph showing the percentage increase in the normalized acoustic intensity of glucose over water versus glucose concentration for various laser wavelengths.

FIG. 8 is a graph 90 showing the percentage increase in the normalized photoacoustic intensity of glucose over water versus glucose concentration for various excitation wavelengths. The photoacoustic intensity is approximately linearly proportional to the glucose concentration over a 20-fold variation in concentration. The increase in photoacoustic intensity 92 over water is about 7.7% at about 4000 mg/dl for an excitation wavelength of 2147 nm.

The present experimental arrangement, without aid from a data-analysis algorithm, demonstrated the ability to measure the glucose concentration to about 200 mg/dl. The detection sensitivity can be improved by a factor of about 2.1 by switching to an excitation wavelength of approximately 1600 nm, as shown in FIG. 5. Furthermore, any experimental error shown in FIG. 8 is caused mainly by the variation in the laser pulse energy. Pulse-to-pulse variation in the current Co:MgF$_2$ laser is quite high, about 10 to 20%. The measurement sensitivity can be further improved substantially by use of a more stable laser. A diode laser is known to be very stable with fluctuation of less than about 0.1% over a long period of several tens of minutes. By extrapolating the preliminary data to what can be expected with a diode laser at about 1600 nm, the high sensitivity needed for a physiological concentration range of interest, from about 30 to 400 mg/dl, can be achievable.

It will be appreciated by persons skilled in the art that the present invention is not limited to what has been shown and described hereinabove, nor the dimensions of sizes of the physical implementation described immediately above. The scope of invention is limited solely by the claims which follow.

What is claimed is:

1. An apparatus for determining a concentration of a component in a subcutaneous bodily fluid, comprising:
    a source for irradiating a portion of a subcutaneous bodily fluid by heat-diffusion to generate acoustic energy propagating in a medium over a surface of said subcutaneous bodily fluid in response to said irradiation;
    a detector comprising a measuring cell and a reference cell for detecting said acoustic energy and providing an acoustic signal in response to said acoustic energy; and
    a processor for determining a concentration of a component in said subcutaneous bodily fluid in response to said acoustic signal and characteristics of said component.

2. The apparatus claimed in claim 1 wherein said component comprises blood glucose.

3. The apparatus claimed in claim 1 wherein said bodily fluid exists within an inner lip.

4. The apparatus claimed in claim 1, wherein said second medium comprises air.

5. The apparatus claimed in claim 1, wherein said source further comprises a laser.

6. The apparatus claimed in claim 1, wherein said source provides electromagnetic energy at wavelengths corresponding to the absorption characteristics of said component.

7. The apparatus claimed in claim 6, wherein said component comprises glucose.

8. The apparatus claimed in claim 7, wherein said range of wavelengths is between about 1520 and 1850 nanometers.

9. The apparatus claimed in claim 7, wherein said range of wavelengths is between about 2050 to 2340 nanometers.

10. The apparatus claimed in claim 1, wherein said detector for detecting said acoustic energy and providing an acoustic signal in response to said acoustic energy, further comprises:
    a device for converting said acoustic energy to said acoustic signal disposed externally of said first medium and in contact relation with said second medium for detecting said acoustic energy.

11. The apparatus claimed in claim 10, wherein said device comprises a microphone.

12. The apparatus claimed in claim 1, further comprising:
    a device for recording and averaging said acoustic signal and generating a photoacoustic spectrum of said component.

13. The apparatus claimed in claim 1, wherein said processor for determining the concentration of said component in response to said acoustic signal and characteristics of said component, further comprises:
    an analyzer for analyzing a photoacoustic spectrum of said acoustic signal.

14. The apparatus claimed in claim 1, further comprising:
    a guide for transmitting said irradiation from said source to said first medium.

15. The apparatus claimed in claim 14, wherein said guide further comprises a fiber-optic guide.

16. A method for determining a concentration of a component in a subcutaneous bodily fluid, comprising the steps of:
    irradiating a portion of subcutaneous bodily fluid by heat-diffusion to generate acoustic energy propagating in a medium over a surface of said subcutaneous bodily fluid in response to said irradiation;
    measuring said acoustic energy generated in response to said irradiating step and providing a measured acoustic signal in response to said measured acoustic energy;
    detecting reference acoustic energy and providing a reference acoustic signal in response to said reference acoustic energy;
    measuring a difference in acoustic response between said measured acoustic signal and said reference acoustic signal; and
    determining a concentration of a component in said subcutaneous bodily fluid in response to said measuring and reference acoustic signals, said difference, and characteristics of said component.

17. The method claimed in claim 16, wherein said component comprises blood glucose.

18. The method claim in claim 16, wherein said bodily fluid exists within an inner lip.

19. The method claimed in claim 16, wherein said second medium comprises air.

20. The method claimed in claim 16, wherein said step of irradiating a portion of said bodily fluid by heat-diffusion to generate acoustic energy propagating in said second medium in response to said irradiation, further comprises the step of:
    providing electromagnetic energy at wavelengths corresponding to the absorption characteristics of said component.

21. The method claimed in claim 20, wherein said component comprises glucose.

22. The method claimed in claim 21, wherein said range of wavelengths is between about 1520 and 1850 nanometers.

23. The method claimed in claim 21, wherein said range of wavelengths is between about 2050 to 2340 nanometers.

24. The method claimed in claim 16, wherein said step of detecting said acoustic energy and providing an acoustic signal in response to said acoustic energy, further comprises the step of:

converting said acoustic energy to said acoustic signal utilizing a device disposed externally of said bodily fluid and in contact relation with said second medium for detecting said acoustic energy.

25. The method claimed in claim 16, further comprising the step of:

recording and averaging said acoustic signal and generating a photoacoustic spectrum of said component.

26. The method claimed in claim 16, wherein said step of determining the concentration of said component in response to said acoustic signal and characteristics of said component, further comprises the step of:

analyzing a photoacoustic spectrum of said acoustic signal.

27. The method claimed in 16, filler comprising the step of:

transmitting said irradiation from said source to said subcutaneous bodily fluid utilizing a guide.

28. The method claimed in claim 27, wherein said guide comprises a fiber-optic guide.

29. An apparatus for measuring a concentration of an analyte in a subcutaneous bodily fluid, comprising:

means for providing electromagnetic energy at wavelengths corresponding to the absorption characteristics of an analyte to excite a portion of subcutaneous bodily fluid by heat-diffusion to generate acoustic energy propagating in a medium over a surface of said subcutaneous bodily fluid in response to said excitation;

first detecting means for detecting said acoustic energy and providing a first acoustic signal in response to said acoustic energy;

second detecting means for detecting noise and providing a second acoustic signal in response to said noise;

means for measuring the difference in acoustic response of said first detecting means and said second detecting means; and means for determining a concentration of said analyte in response to said first acoustic signal, said second acoustic signal, said difference, and an absorption spectrum of said analyte.

30. The apparatus claimed in claim 29, wherein said analyte comprises blood glucose.

31. The apparatus claimed in claim 29, wherein said second medium comprises air.

32. A method of measuring a concentration of an analyte in a subcutaneous bodily fluid, comprising the steps of:

providing electromagnetic energy at wavelengths corresponding to the absorption characteristics of an analyte to excite a portion of subcutaneous bodily fluid by heat-diffusion to generate acoustic energy propagating in a medium over a surface of said subcutaneous bodily fluid in response to said excitation;

detecting said acoustic energy by a measuring cell and providing a first acoustic signal in response to said acoustic energy;

detecting noise by a reference cell and providing a second acoustic signal in response to said noise;

receiving said first acoustic signal from said measuring cell;

receiving said second acoustic signal from said reference cell;

measuring the difference in acoustic response from said measuring cell and said reference cell; and determining a concentration of said analyte in response to said first acoustic signal said second acoustic signal, said difference, and an absorption spectrum of said analyte.

33. The method claimed in claim 32, wherein said analyte comprises blood glucose.

34. The method claimed in claim 32, wherein said second medium comprises air.

35. The method claimed in claim 32, wherein said step of determining said concentration in response to said acoustic signal and absorption spectrum of said analyte, further comprises the step of:

generating a photoacoustic spectrum of said analyte.

36. An apparatus for determining a concentration of glucose in a subcutaneous body part, comprising:

a source for irradiating a portion of a subcutaneous body part by heat diffusion to generate acoustic energy propagating in air over a surface of said subcutaneous body part in response to said irradiation;

a detector comprising a measuring cell and a reference cell for detecting said acoustic energy and providing an acoustic signal in response to said acoustic energy; and a processor for determining a concentration of glucose in said subcutaneous body art in response to said acoustic signal and characteristics of glucose.

37. The apparatus claimed in claim 36, wherein said body part comprises an inner lip.

38. The apparatus claimed in claim 36, wherein said source further comprises a laser.

39. The apparatus claimed in claim 36, wherein said source provides electromagnetic energy at wavelength ranges corresponding to the absorption characteristics of said glucose.

40. The apparatus claimed in claim 39, wherein said range of wavelengths is between about 1520 and 1850 nanometers.

41. The apparatus claimed in claim 39, wherein said range of wavelengths is between about 2050 to 2340 nanometers.

42. The apparatus claimed in claim 36, wherein said detector for detecting said acoustic energy and providing an acoustic signal in response to said acoustic energy, further comprises:

a device for converting said acoustic energy to said acoustic signal disposed externally of said body part and in contact relation with said air for detecting said acoustic energy.

43. The apparatus claimed in claim 42, wherein said device comprises a microphone.

44. The apparatus claimed in claim 36, further comprising:

a device for recording and averaging said acoustic signal and generating a photoacoustic spectrum of said glucose.

45. The apparatus claimed in claim 36, wherein said processor for determining the concentration of glucose in said subcutaneous body part in response to said acoustic signal and characteristics of glucose, further comprises:

an analyzer for analyzing a photoacoustic spectrum of said acoustic signal.

46. The apparatus claimed in claim 36, further comprising:

a guide for transmitting said irradiation from said source to said body part.

47. The apparatus claimed in claim 46, wherein said guide further comprises a fiber-optic guide.

48. A method for determining a concentration of glucose in a subcutaneous body part, comprising the steps of:

irradiating a portion of a subcutaneous body part by heat-diffusion to generate acoustic energy propagating in air over a surface of said body part in response to said irradiation;

detecting said acoustic energy by a measuring cell and providing a first acoustic signal in response to said acoustic energy;

detecting noise by a reference cell and providing a second acoustic signal in response to said noise;

receiving said first acoustic signal from said measuring cell;

receiving said second acoustic signal from said reference cell;

measuring the difference in acoustic response from said measuring cell and said reference cell; and determining a concentration of glucose in said subcutaneous body part in response to said first acoustic signal, said second acoustic signal, said difference, and characteristics of glucose.

49. The method claimed in claim 48, wherein said body part comprises an inner lip.

50. The method claimed in claim 48, wherein said step of irradiating a portion of said body part by heat-diffusion to generate acoustic energy propagating in air over a surface of said body part in response to said irradiation, further comprises the step of:

providing electromagnetic energy at wavelengths corresponding to the absorption characteristics of said glucose.

51. The method claimed in claim 50, wherein said range of wavelengths is between about 1520 and 1850 nanometers.

52. The method claimed in claim 50, wherein said range of wavelengths is between about 2050 to 2340 nanometers.

53. The method claimed in claim 48, wherein said step of detecting said acoustic energy and providing an acoustic signal in response to said acoustic energy, further comprises the step of:

converting said acoustic energy to said acoustic signal utilizing a device disposed externally of said subcutaneous body part and in contact relation with said air for detecting said acoustic energy.

54. The method claimed in claim 48, further comprising the step of:

recording and averaging said acoustic signal and generating a photoacoustic spectrum of said glucose.

55. The method claimed in claim 48, wherein said step of determining the concentration of said glucose in response to said acoustic signal and characteristics of said glucose, further comprises the step of:

analyzing a photoacoustic spectrum of said acoustic signal.

56. The method claimed in claim 48, further comprising the step of:

transmitting said irradiation from said source to said body part utilizing a guide.

57. The method claimed in claim 56, wherein said guide comprises a fiber-optic guide.

\* \* \* \* \*